United States Patent [19]
Blenke et al.

[11] Patent Number: 5,525,175
[45] Date of Patent: Jun. 11, 1996

[54] APPARATUS AND METHOD FOR APPLYING A CURVED ELASTIC TO A MOVING WEB

[75] Inventors: Timothy J. Blenke, Neenah; James F. Hyatt, Appleton, both of Wis.

[73] Assignee: Kimberly-Clark Corporation, Neenah, Wis.

[21] Appl. No.: 250,230

[22] Filed: May 27, 1994

[51] Int. Cl.⁶ .............................. A61F 13/15; A41B 13/04
[52] U.S. Cl. ..................... 156/161; 156/163; 156/164; 156/229; 156/494; 604/385.2
[58] Field of Search ............................. 156/161, 163, 156/164, 229, 494; 604/385.2

[56] References Cited

U.S. PATENT DOCUMENTS

| | | |
|---|---|---|
| 4,293,367 | 10/1981 | Klasek et al. . |
| 4,618,384 | 10/1986 | Sabee . |
| 4,626,305 | 12/1986 | Suzuki et al. ............... 156/229 X |
| 4,666,542 | 5/1987 | de Jonckheere ............... 156/164 |
| 4,762,582 | 8/1988 | de Jonckheere ............... 156/164 |
| 4,801,345 | 1/1989 | Dussaud et al. . |
| 4,915,767 | 4/1990 | Rajala et al. . |
| 4,917,746 | 4/1990 | Kons et al. . |
| 5,147,487 | 9/1992 | Nomura et al. . |
| 5,275,676 | 1/1994 | Rooyakkers et al. . |
| 5,389,173 | 2/1995 | Merkatoris et al. ............... 156/164 |

FOREIGN PATENT DOCUMENTS

| | | |
|---|---|---|
| 0409876 | 7/1993 | European Pat. Off. . |
| 61-152801 | 7/1986 | Japan .................... 156/161 |
| 2248380 | 4/1992 | United Kingdom . |

*Primary Examiner*—Jeff H. Aftergut
*Attorney, Agent, or Firm*—Kimberly-Clark Corp.

[57] ABSTRACT

A distinctive apparatus and method for applying an elastic strand onto a moving substrate along a selected curvilinear path includes a transporting mechanism for moving the substrate along a selected substrate path and a supplying mechanism for supplying the elastic strand along a selected elastic path. An oscillating mechanism selectively changes a positioning of the elastic strand and includes a slidably movable guide which moves in a direction essentially transverse to said substrate path. The elastic strand slidably travels along the guide which positions the elastic strand such that the elastic strand is selectively applied to the substrate along the curvilinear path. A bonding mechanism selectively applies adhesive in an arrangement which selectively secures the elastic strand to the substrate. A rotatable nip roll contacts the elastic strand and the substrate to press the elastic strand onto the substrate along the curvilinear path.

20 Claims, 8 Drawing Sheets

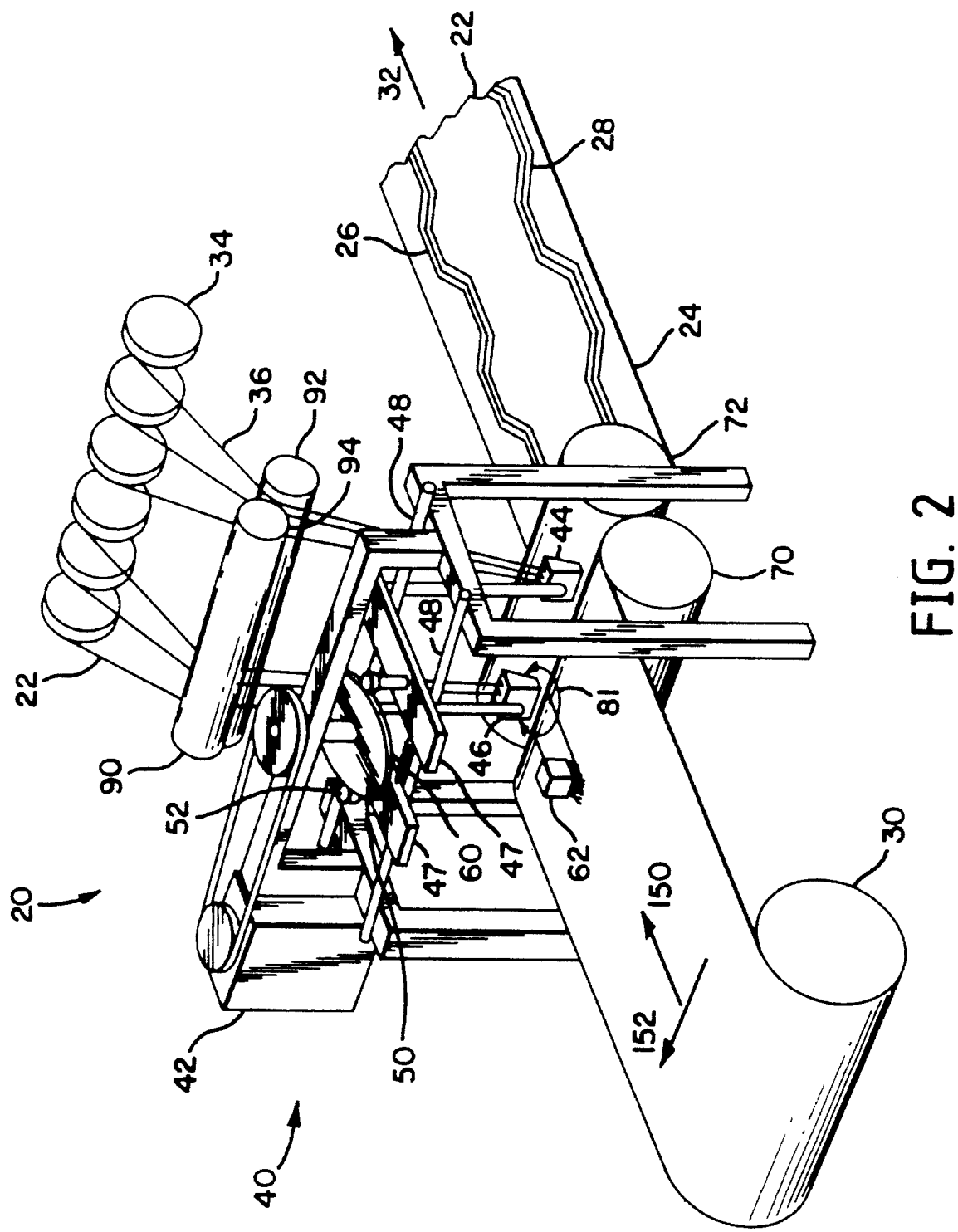

APPARATUS AND METHOD FOR APPLYING A CURVED ELASTIC TO A MOVING WEB

BACKGROUND OF THE INVENTION

1. Technical Field

The present invention relates to an apparatus and method for applying at least one elastic strand onto a moving substrate web along a curved path. More particularly, the present invention relates to an apparatus and method for applying elastic strands in a curved configuration at each of the leg opening regions of a disposable absorbent article, such as a disposable diaper.

2. Description of the Related Art

Absorbent articles, such as disposable diapers, training pants, adult incontinence articles and the like, have incorporated elasticized gathers at the leg openings of the article to help contain body exudates. The leg openings are positioned at the lateral side margins of the article and can be elasticized with a single elastic member or with multiple elastic members. Various techniques for applying multiple elastic strands onto a substrate are well known to those skilled in the art.

It has been desirable to employ elastic members which are curved to better follow the contours of the leg openings formed in the side margins of disposable absorbent articles. The curved elastic members improve the ability of the article to contain body exudates. Various techniques for applying curved elastic members onto a substrate are well known to those skilled in the art. For example, techniques for applying an elastic member to a substrate web along a curved pattern have been described in U.S. Pat. No. 4,915,676 issued Apr. 10, 1990, to Rajala et al. and U.S. Pat. No. 5,275,676 issued Jan. 4, 1994, to Rooyakkers et al.

However, some conventional techniques for applying curved elastic members, such as described above, have not provided an adequate system for efficiently placing an elastic member along a desired curvilinear path on the surface of a moving substrate. Typically, conventional techniques have incorporated complicated web paths for the elastic members which include oscillations of great magnitude such that the desired curvature can be maintained. Moreover, conventional techniques have not adequately maintained the desired spacing between the individual elastic strands when multiple strands of elastomeric material are applied to a substrate web along a curvilinear path. Further, the complicated web paths of conventional techniques have not provided an efficient method to thread the elastic members.

SUMMARY OF THE INVENTION

In response to the discussed difficulties and problems encountered in the prior art, a new apparatus and method for applying an elastic member to a substrate along a curvilinear path has been discovered.

The present invention provides a distinctive apparatus and method for applying at least one elastic strand onto a continuously moving substrate along a selected curvilinear path. The apparatus comprises a transporting means for moving the substrate along a substrate path and a supplying means for providing the elastic strand along an elastic path. An oscillating means selectively changes a positioning of the elastic strand and includes a slidably movable guide which is configured to move in a direction essentially transverse to the substrate path. The elastic strand slidably travels along the guide as the guide moves such that the elastic strand follows a curvilinear path. A bonding means selectively applies an adhesive in an arrangement which secures the elastic strand to the substrate along the curvilinear path. A pair of rotatable nip rolls, which are adapted to be in rolling engagement with the substrate, are configured to press the elastic strand onto the substrate to maintain the elastic strand on the substrate along the curvilinear path.

In another aspect, the present invention concerns an apparatus for applying a first plurality of elastic strands onto a substrate along a first curvilinear path and a second plurality of elastic strands onto the substrate along a second curvilinear path. The apparatus comprises a transporting means for moving the substrate along a substrate path and a supplying means for providing the first and the second plurality of elastic strands along an elastic path. A first slidably movable guide, along which the first plurality of elastic strands slidably travel, includes a first cam follower which cooperates with a rotatable cam. The first guide is configured to slidably move in a direction essentially transverse to the substrate path as the cam rotates such that the first plurality of elastic strands follow the first curvilinear path. A second slidably movable guide, along which the second plurality of elastic strands slidably travel, includes a second cam follower which also cooperates with the cam. The second guide is configured to slidably move in a direction essentially transverse to the substrate path as the cam rotates such that the second plurality of elastic strands follow the second curvilinear path. A bonding means applies an adhesive in an arrangement which selectively secures the first and second plurality of elastic strands to the substrate along the first and said second curvilinear paths. A pair of rotatable nip rolls, which are adapted to be in rolling engagement with the substrate, press the first and second plurality of elastic strands onto the substrate to maintain the first and second plurality of elastic strands on the substrate along the first and second curvilinear paths.

A process aspect of the invention provides a method for applying at least one elastic strand onto a continuously moving substrate along a curvilinear path. The method comprises the steps of moving the substrate along a substrate path and supplying the elastic strand along an elastic path. The elastic strand is delivered onto the substrate along the curvilinear path. The elastic strand is moved by a slidably movable guide in a direction essentially transverse to the substrate path. The guide has at least one groove therein which has a depth sufficient to contain and slidably guide the elastic strand. An adhesive is applied in an arrangement which selectively secures the elastic strand to the substrate along the curvilinear path. The elastic strand is pressed onto the substrate with a rotatable nip roll to maintain the elastic strand on the substrate along the curvilinear path.

In particular aspects, the apparatus and method of the present invention can be configured to apply two or more pluralities of elastic strands onto selected side edge portions of the substrate along curvilinear paths that may or may not be in a parallel configuration. The apparatus and method of the invention can also be configured to maintain a substantially constant spacing between the elastic strands when a plurality of elastic strands are secured to the substrate along the curvilinear path. In other aspects of the invention, the elastic strand may be variably elongated before it is selectively secured to the substrate. For example, the elastic strand may be constrictively passed between a pair of variable speed drive rolls which are rotated at a variable speed to variably elongate the elastic strand.

The various aspects of the apparatus and method of the present invention can more reliably and efficiently apply an elastic strand along a selected curvilinear path across the surface of a substrate. The invention can avoid the use of complicated web paths that are more difficult to thread and maintain. Particular aspects of the invention can accommodate a variety of techniques for selectively applying adhesive onto the elastic strands or onto the substrate. Where a plurality of spaced apart elastic strands are selectively applied to a substrate, the invention can be configured to more effectively maintain the desired spacings between the individual elastic strands.

BRIEF DESCRIPTION OF THE DRAWINGS

The present invention will be more fully understood and further advantages will become apparent when reference is made to the following detailed description of the invention and the drawings, in which:

FIG. 2 representatively shows a perspective view of one example of an apparatus of the present invention;

DETAILED DESCRIPTION OF THE INVENTION

The present invention provides an apparatus and method for applying an elastic strand onto a continuously moving substrate web along a curvilinear path. The apparatus and method are particularly useful for applying a plurality of elastic strands in a curved configuration at each of the leg opening regions of a disposable absorbent article, such as a disposable diaper. It is readily apparent, however, that the apparatus and method would be suitable for applying at least one elastic strand along a curvilinear path onto any substrate or absorbent article such as adult incontinence products, feminine care products, training pants and the like.

Figure 1:
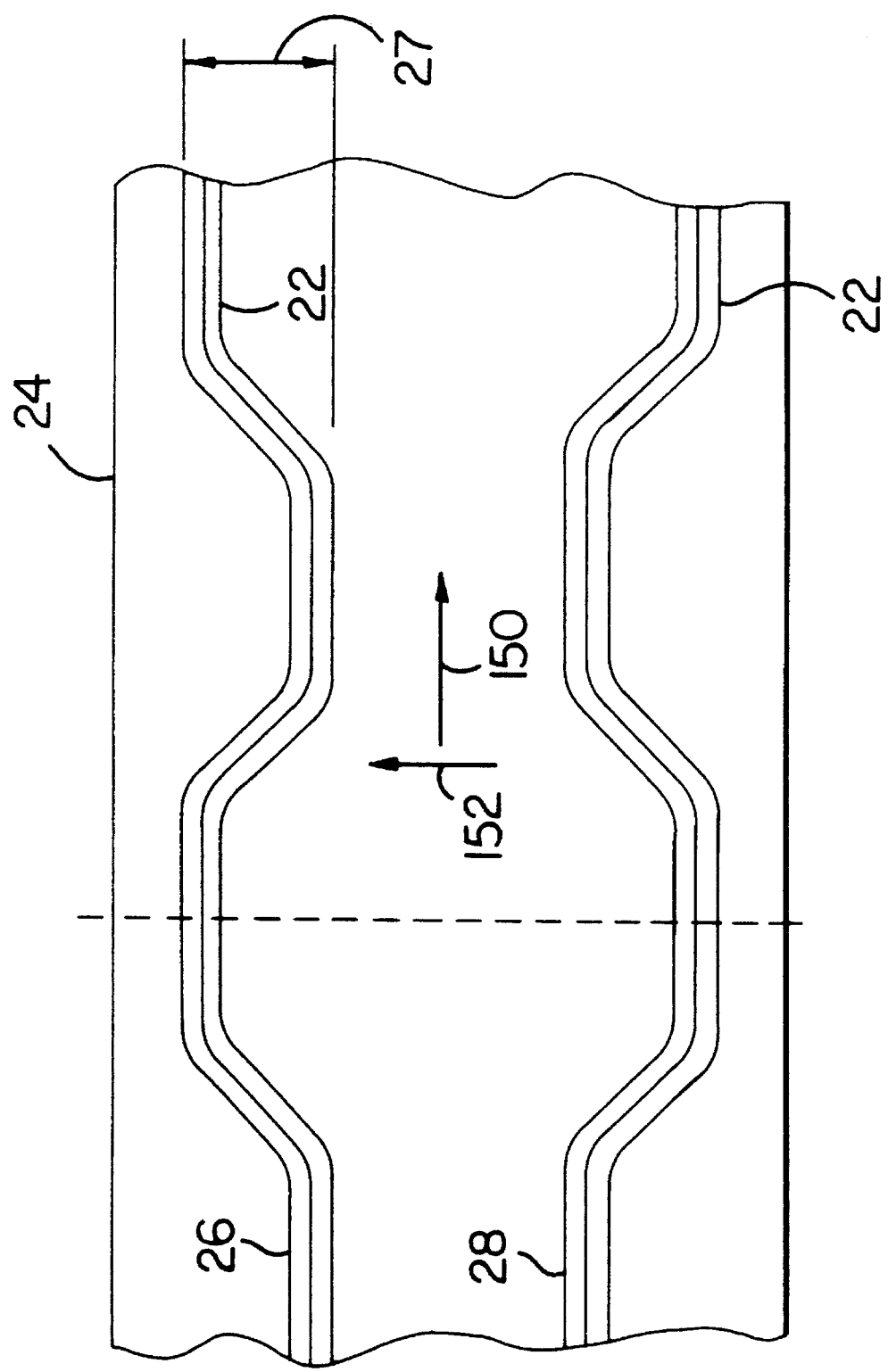
FIG. 1 representatively shows a plan view of a substrate which incorporates a first plurality of elastic strands applied along a first curvilinear path and a second plurality of elastic strands applied along a second curvilinear path.

The present invention can best be understood by reference to the drawings in which like numerals represent like elements. FIG. 1 illustrates a substrate web having a plurality of elastic strands applied thereto along a selected curvilinear path along both side edge regions of the substrate. As illustrated in FIG. 1, a plurality of elastic strands 22 are secured to a substrate web 24 along curvilinear paths 26 and 28. Desirably, the elastic strands 22 are secured to the side edge regions of the substrate 24. The curvilinear paths 26 and 28 may be parallel or may be independent of one another. Desirably, the curvilinear paths 26 and 28 intermittently converge and diverge from each other such that the elastic strands 22 can be used along the leg opening regions of an absorbent article. In this configuration, the elastic strands 22 can be substantially symmetrically disposed relative to a longitudinal centerline of the substrate web 24. As such, the curvilinear path 26 is approximately a mirror image of the oppositely positioned curvilinear path 28.

The elastic strands 22 suitably comprise any elastomeric material capable of being elongated at least about 50 percent, desirably about 350 percent, and capable of recovering to within at least about 250 percent, desirably about 150 percent of its original length after being elongated about 300 percent. In one specific embodiment the elastic strands 22 can, for example, be composed of Lycra® strands commercially available from Dupont Corp. Alternatively, the elastic strands 22 can be composed of a natural or synthetic rubber, a thermoplastic elastomer or a heat activatable elastic material.

A wide range of materials are suitable for use as the substrate web 24 as representatively illustrated in FIG. 1. For example, the substrate 24 can include a nonwoven material such as a spunbond, meltblown, spun laced or carded polymeric material, a film material such as a polyolefin or polyurethane film, a foam material or combinations thereof. The substrate web 24 can then be used in the manufacture of absorbent articles such as diapers, training pants, feminine care products, adult incontinence products and the like. The elastic strands 22 can also be applied directly onto a substrate web of the absorbent articles. In a specific embodiment, a plurality of elastic strands 22 are selectively applied to a web of diapers along selected curvilinear paths.

For the purposes of the present description, the various aspects of the apparatus and method of the present invention will be described as being used to apply a plurality of elastic strands onto a continuously moving substrate along two selected curvilinear paths. For example, when constructing an absorbent article, such as a disposable diaper, it may be desirable to apply a plurality of elastic strands onto each of the side edge portions of the substrate web. However, it should be readily understood that the apparatus and method of the present invention can also be used to apply one elastic strand along a single curvilinear path or a plurality of elastic strands along a plurality of curvilinear paths onto any substrate. For example, the present invention may be used to apply from one to about 10 elastic strands and desirably from about 3 to about 5 elastic strands onto the substrate along the curvilinear paths.

As representatively illustrated in FIG. 2, the apparatus, as generally indicated at 20, and method of the invention includes a transporting means 30 for moving the substrate 24 along a substrate path 32 in a machine direction 150. As used herein and at any particular location along the apparatus or method, the machine direction is the direction along which the substrate 24 is intended to move. The cross machine direction 152 is perpendicular to the local machine direction and parallel to the plane of the substrate 24. The z-direction is perpendicular to the plane of the substrate 24. The transporting means 30 may be any means known to those skilled in the art such as, for example, a substrate conveyor. The apparatus 20 also includes a supplying means 34 for supplying the elastic strands 22 along an elastic path 36. For example, the supplying means 34 may include a pair of driven rolls 92 and 94. An elastic applicating unit, generally indicated at 40, is configured to apply the elastic strands 22 to the continuously moving substrate 24 along the curvilinear paths 26 and 28.

The elastic applicating unit 40, as representatively illustrated in FIG. 2, includes an oscillating means 42 for selectively changing a positioning of the elastic strands 22 along the cross machine direction 152 of the apparatus 20. The supplying means 34 is configured to deliver the elastic strands 22 to the oscillating means 42 which, in turn, is configured to deliver the elastic strands 22 to a pair of nip rolls 70 and 72 along the curvilinear paths 26 and 28. A bonding means 62 is configured to selectively apply an adhesive in an arrangement which secures the elastic strands 22 to the substrate 24 along the curvilinear paths 26 and 28. The rotatable nip rolls 70 and 72 are adapted to be in rolling engagement with the substrate 24 and are configured to press the elastic strands 22 onto the substrate 24 to maintain the elastic strands 22 on the substrate 24 along the curvilinear paths 26 and 28.

As representatively illustrated in FIG. 2, the oscillating means 42 includes a pair of slidably movable guides 44 and 46 which are connected to a pair of guide supports 47. The movable guides 44 and 46 are located along the elastic path 36 such that the elastic strands 22 slidably travel along the movable guides 44 and 46. The movable guides 44 and 46 and guide supports 47 are configured to slidably move along the parallel slides 48 in a direction essentially transverse to the substrate path 32 such that the elastic strands 22 follow the curvilinear paths 26 and 28. Thus, in use, the movable guides 44 and 46 and guide supports 47 move in the cross machine direction 152. The movable guides 44 and 46 and the guide supports 47 may be configured to slidably move in the cross machine direction 152 by any suitable means known to those skilled in the art. For example, the guide supports 47 may be slidably connected to a pair of parallel slides 48 using suitable means such as a pair of conventional slide bearings. Alternatively, the guide supports 47 may be configured to slidably move on conventional roller bearings along a linear track as is well known to those skilled in the art. When applying the elastic strands to an absorbent article, such as a diaper, the oscillating means 42 and movable guides 44 and 46 are configured to supply the elastic strands 22 along the curvilinear paths 26 and 28 with each cycle in the curvilinear path corresponding to the length of each individual article.

The movable guides 44 and 46 may be made from any material known to those skilled in the art. Desirably, the movable guides 44 and 46 are made from a polytetrafluoroethylene material or a ceramic material. The movable guides 44 and 46, as representatively illustrated in FIGS. 2–3, can include a plurality of spaced apart grooves 54 which extend along a length 57 of the guides 44 and 46 in a direction essentially parallel to the elastic path 36. Each of the grooves 54 is configured to accept therein an individual elastic strand 22. The grooves 54 have a depth 56 which is sufficient enough to contain and slidably guide the elastic strands 22 as the movable guides 44 and 46 move in the cross machine direction 152. For example, the grooves 54 may have a depth 56 of from about 0.5 centimeters to about 2.0 centimeters. The grooves 54 are configured to provide a desired spaced apart distance between the individual elastic strands 22. For example, as illustrated in FIG. 3, the guides 44 and 46 may slidably guide three individual elastic strands 22 with adjacent strands being spaced apart by a distance of from about 0.2 to about 0.5 centimeters. It should be readily apparent that the guides 44 an 46 should have an appropriate number of grooves 54 therein to correspond to the number of elastic strands 22. For example, the movable guides 44 and 46 may have from one groove to about 10 grooves therein to contain the elastic strands 22. In addition, as representatively illustrated in FIG. 3, the grooves 54 can include a widened out portion 58 at an innermost depth of said grooves 54 to better contain the elastic strands 22 within the movable guides 44 and 46. The grooves 54 in the movable guides 44 and 46 allow for the efficient threading of the elastic strands 22 which helps increase the efficiency of the apparatus 20.

The slidably movable guides 44 and 46 also have a length 57 as representatively illustrated in FIG. 3. The length 57 can be controlled to provide the desired placement of the elastic strands 22 along the curvilinear paths 26 and 28. For example, the length 57 of the movable guides 44 and 46 is at least about 3 centimeters, desirably from about 4 to about 8 centimeters and more desirably from about 4 to about 6.3 centimeters. As the length 57 decreases, the guides 44 and 46 are undesirably required to oscillate over a greater magnitude to ensure that the elastic strands 22 follow the curvilinear paths 26 and 28. Moreover, as the length 57 decreases, it becomes increasingly difficult to maintain the elastic strands 22 within the grooves 54 of the movable guides 44 and 46.

The movable guides 44 and 46 are connected to the guide supports 47 by any suitable means such as welding, clamping or fastening using mechanical fasteners such as screws or bolts. The guide supports 47 may then be connected to the parallel slides 48. The parallel slides can be any slides known to those skilled in the art. For example, the parallel slides 48 can be #100 bar slides distributed by Precision Lamination, Inc., a business having offices located in Rockford, Illinois. The guide supports 47 can be connected to the parallel slides 48 using conventional slide bearings such as #979100 nylaglide linear bearings also distributed by Precision Lamination, Inc.

In one aspect of the invention, the oscillating means 42, as representatively illustrated in FIG. 2, can include a rotatable cam 50 located between the guide supports 47 and a pair of cam followers 52 which are connected to the guide supports 47 and slidably contact the cam 50 as it is rotated. At least one extension spring 60 extends between and is connected to the guide supports 47 to maintain the sliding contact between the cam followers 52 and the cam 50. In operation, the rotatable cam 50 is rotated and the guide supports 47 and movable guides 44 and 46 are moved about the parallel slides 48 through a predetermined periodic pattern such that the elastic strands 22 follow the curvilinear paths 26 and 28. The cam 50 can be configured such that the movable guides 44 and 46 are capable of simultaneously moving in opposite directions along the parallel slides 48. Suitable cams are well known to those skilled in the art. Vendors are able to design and produce suitable cams once they are advised of particular operational parameters. Pertinent parameters can include, for example, the dimensions and inertia of the moving components, the desired number of cycles per minute, and the particular curvilinear path desired.

The rotatable cam 50 can be driven by any means known to those skilled in the art. For example, as representatively illustrated in FIG. 2, the rotatable cam 50 can be driven by an electric motor suitably connected to the cam by a system of belts and pulleys. Suitable electric motors are well known to those skilled in the art. Alternatively, the rotatable cam 50 can be operably coordinated to the movement of another device such as, for example, the transporting means 30 or the nip rolls 70 and 72.

Figure 2A:
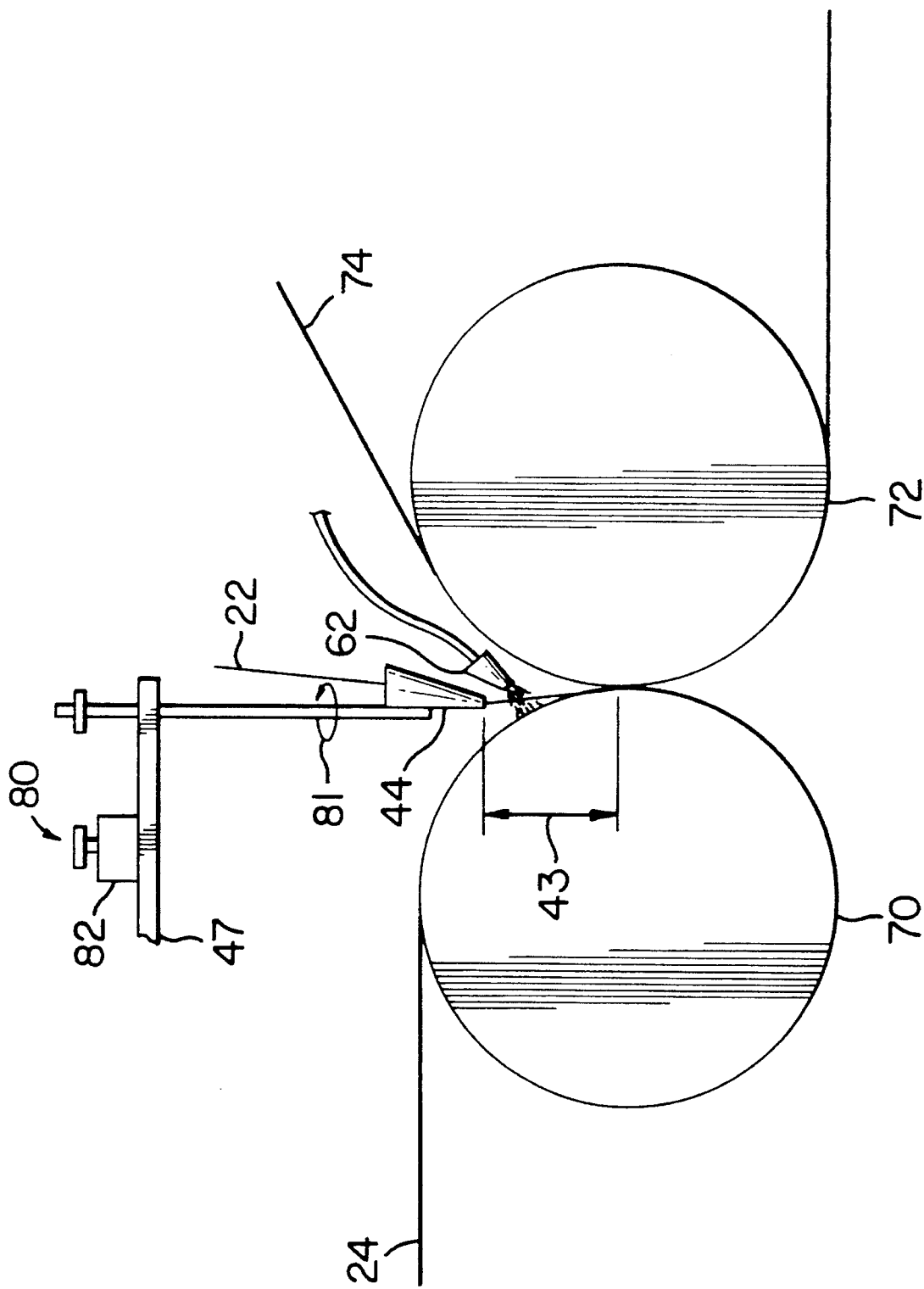
FIG. 2A representatively shows a partial side elevational view of the apparatus shown in FIG. 2.

As representatively illustrated in FIGS. 2 and 2A, the elastic applicating unit 40 includes a bonding means 62 which is used to selectively secure the elastic strands 22 to the substrate 24 along the curvilinear paths 26 and 28. Various techniques may be employed to secure the elastic strands 22 onto the substrate 24. For example, a desired attachment may be provided by adhesive bonding, thermal bonding, ultrasonic bonding or the like. As representatively illustrated in FIGS. 2 and 2A, the elastic strands 22 may be adhered to the substrate 24 with a hot melt, pressure sensitive adhesive, such as a H2096 adhesive available from Findley Adhesives Company, a business having offices at Wauwatosa, Wi. The selected hot melt adhesive is deposited by the bonding means 62 in an arrangement which secures the elastic strands 22 onto the substrate 24. The adhesive arrangement is configured to substantially avoid contact with the nip rolls 70 and 72. For example, the bonding means 62 may deposit a swirl pattern of overlapping loops of hot melt adhesive onto the elastic strands 22 or onto the substrate 24. In a particular aspect, as representatively illustrated in FIG. 2A, the adhesive is applied directly onto the elastic strands 22 before the elastic strands 22 contact the substrate 24. The adhesive may be applied such that it covers substantially the entire outer peripheral surface of the elastic strands 22. For example, the adhesive may be deposited onto the elastic strands 22 such that it wraps completely around each elastic strand 22. In this configuration, the adhesive overspray may be contained on the substrate 24 which is positioned directly behind and underneath the elastic strands 22. Alternatively, the adhesive can be applied directly onto the substrate 24 before the elastic strands 22 contact the substrate 24. The adhesive may also be applied intermittently to either the elastic strands 22 or the substrate 24.

In another aspect of the invention as representatively illustrated in FIG. 2A, a second substrate web 74 may be fed into the nip rolls 70 and 72 such that the elastic strands 22 are disposed between the substrate webs 24 and 74. In such a configuration, the adhesive may be applied on the elastic strands 22, the substrate 24, the second substrate 74, or any combination thereof. The combination of substrate webs 24 and 74 effectively isolates the nip rolls 70 and 72 from any adhesive overspray. A wide range of materials are suitable for the second substrate web 74 such as, for example, those described above in reference to substrate web 24.

It has been found that the securement location of the elastic strands 22 onto the substrate 24 can more closely match the cross-directional positioning of the movable guides 44 and 46 and the curvilinear paths 26 and 28 when the distance 43, as representatively illustrated in FIG. 2A, between the guides 44 and 46 and a position where the elastic strands 22 contact the substrate 24 and the nip rolls 70 and 72 is kept to a minimum. Accordingly, when the distance 43 is kept relatively small, the securement of the elastic strands 22 on the substrate 24 more closely matches the cross-directional location and movement of the guides 44 and 46 as they are moved by the rotatable cam 50. If the distance 43 between the guides 44 and 46 and the nip rolls 70 and 72 and the substrate 24 is too great, the correspondence between the cross-directional positioning of the guides 44 and 46 and the curvilinear paths 26 and 28 on the substrate 24 may be more difficult to maintain. Moreover, as the distance 43 increases, the guides 44 and 46 are undesirably required to oscillate over a greater magnitude to ensure that the elastic strands 22 follow the curvilinear paths 26 and 28.

In particular aspects of the invention, the distance 43 between the guides 44 and 46 and the position where the elastic strands 22 contact the substrate 24 and nip rolls 70 and 72, as representatively illustrated in FIG. 2A, is from about 0.25 to about 11 centimeters, desirably the distance 43 is from about 0.25 to about 5 centimeters, more desirably the distance 43 is less than 2 centimeters, and even more desirably the distance 43 is less than 1 centimeter. Particular aspects of the invention can include a means for adjusting the distance 43 between the guides 44 and 46 and the substrate 24 and nip rolls 70 and 72. For example, the movable guides 44 and 46 may be slidably connected to a shaft which is connected to the guide supports 47 and extends towards the nip rolls 70 and 72. The guides 44 and 46 can be selectively positioned and locked in place at predetermined locations along the length dimension of the shaft.

Figure 2B:
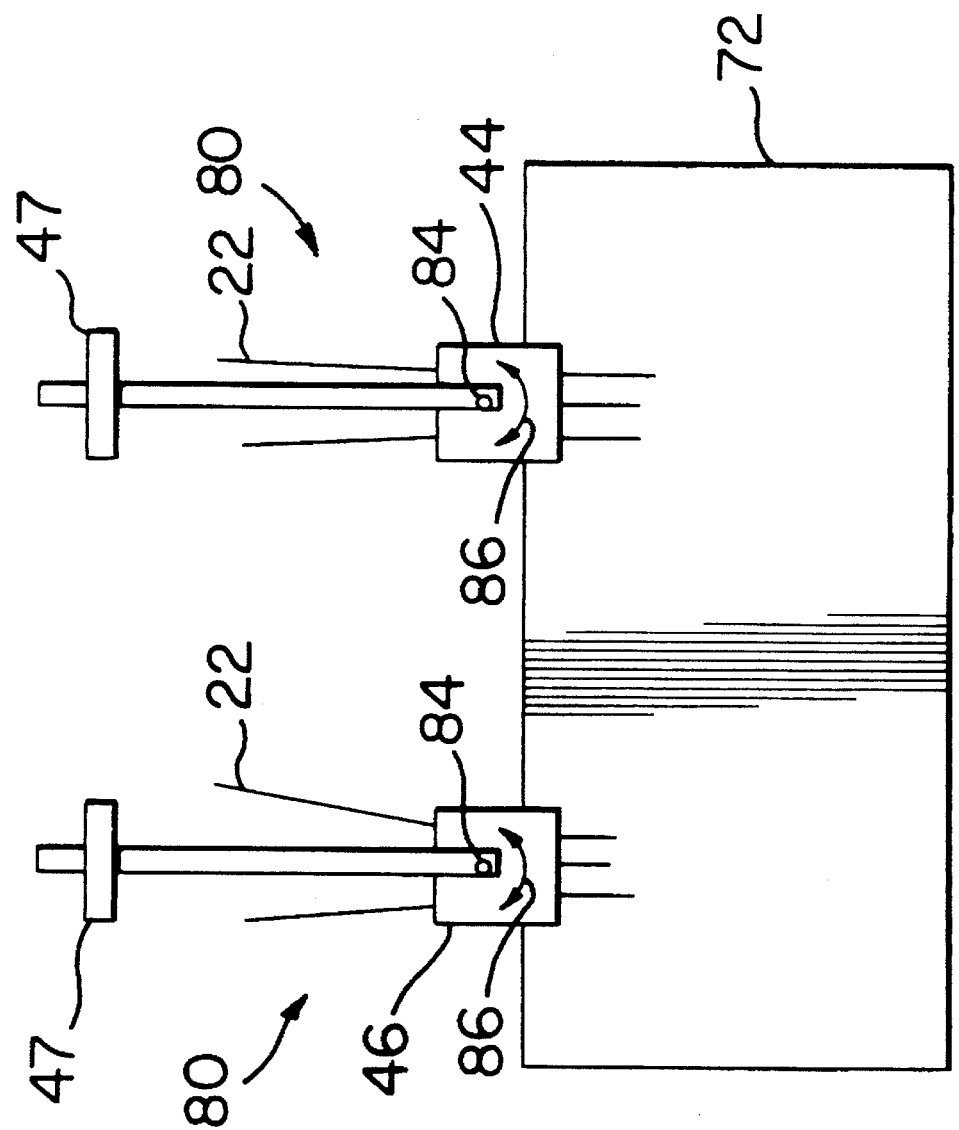
FIG. 2B representatively shows a partial elevational view of the apparatus shown in FIG. 2 taken along the machine direction.
Figure 3:
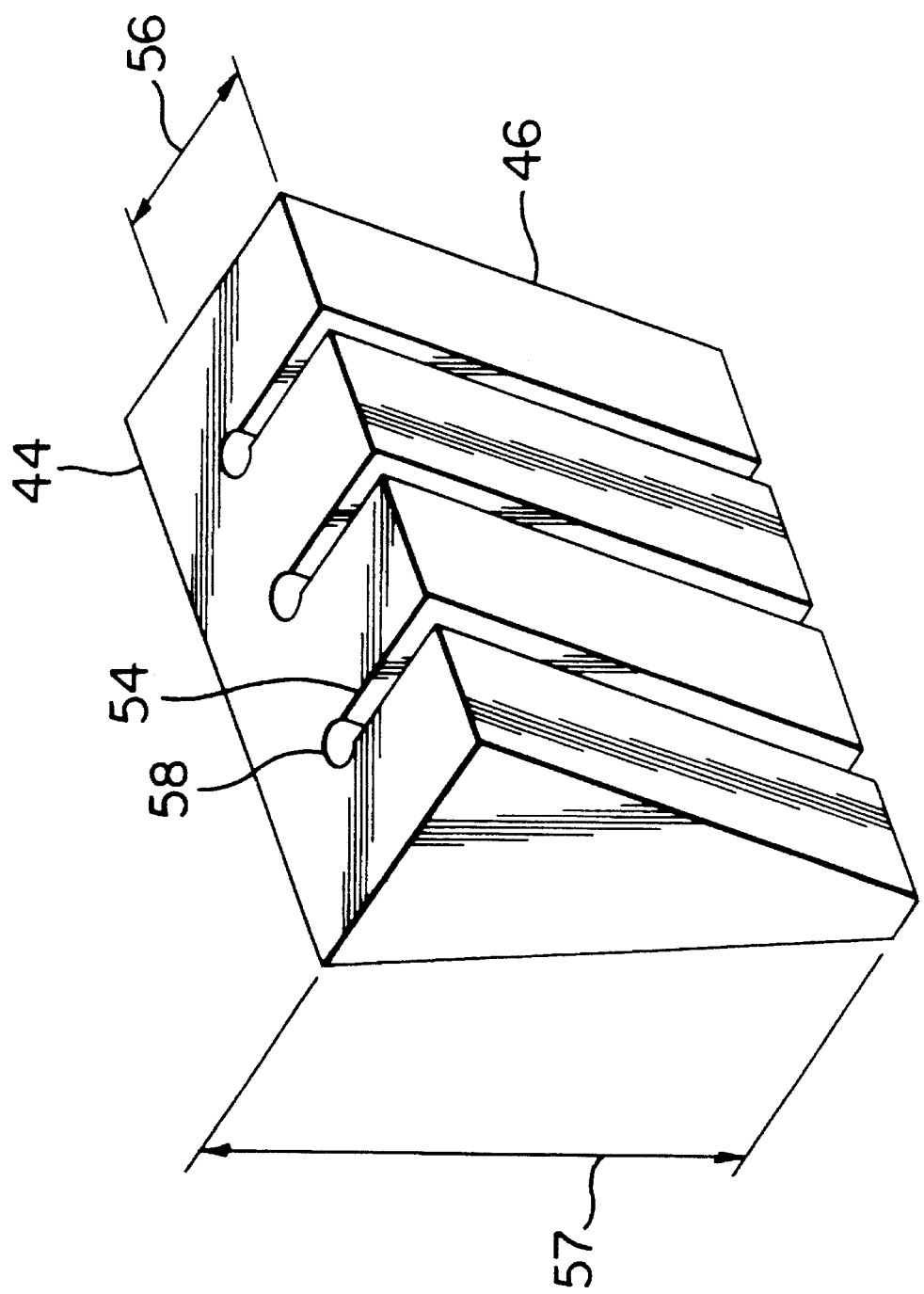
FIG. 3 representatively shows a perspective view of one example of the guide of the apparatus illustrated in FIG. 2.

The oscillating means 42 of the present invention, as representatively illustrated in FIGS. 2–2B, may also include a pivoting means 80 which is configured to selectively rotate the movable guides 44 and 46 as the guides are moved in the cross machine direction 152. As representatively illustrated in FIG. 2A, the pivoting means 80 may be configured to rotate the guides 44 and 46 in the direction indicated by the arrow 81 associated therewith about the z axis and in the plane of the substrate 24, or the x-y plane. As representatively illustrated in FIG. 2B, the pivoting means 80 may also be configured to rotate the guides 44 and 46 in the direction indicated by the arrow 86 associated therewith about the x axis in the y-z plane. The pivoting means 80 may be configured to rotate the guides 44 and 46 such that the spacing between the elastic strands 22 remains substantially constantlas the elastic strands 22 are secured to the substrate 24 along the curvilinear paths 26 and 28.

As representatively illustrated in FIG. 2A, the pivoting means 80 may be configured to cyclically rotate the guides 44 and 46 in the direction indicated by the arrow 81 associated therewith such that a facing surface of the guides 44 and 46 is in a perpendicular relationship to the curvilinear paths 26 and 28 in the x-y plane. Desirably, the perpendicular relationship is maintained to ensure that the spacing between the elastic strands 22 remains substantially constant after they have been secured to the substrate 24. The pivoting means 80 may include an electric motor 82, such as, for example, a servo motor, operatively connected to the guides 44 and 46 to rotate the guides in the direction indicated by the arrow 81 associated therewith. For example, the guides 44 and 46 may be connected to a shaft which is suitably connected to the guide supports 47 using conventional bearings such that the guides are allowed to rotate. The shaft may also be suitably connected through a system of pulleys and a belt to the electric motor 82. In use, the shaft and guides 44 and 46 are cyclically rotated back and forth by the motor 82 in the direction indicated by the arrow 81 associated therewith in the x-y plane to maintain the perpendicular relationship between the facing surface of the guides 44 and 46 and the curvilinear paths 26 and 28.

As representatively illustrated in FIG. 2B, the pivoting means 80 may also be configured to cyclically rotate or pivot the guides 44 and 46 in the direction indicated by the arrow 86 associated therewith such that the spacing between the elastic strands 22 remains substantially constant after they have been secured to the substrate 24. For example, the guides 44 and 46 may be connected to a pivot rod using conventional bearings such that the guides are allowed to rotate or pivot about the pivot rod. The pivot rod may be connected to the shaft, as representatively illustrated in FIG. 2B, which is suitably connected to the guide supports 47. The guides 44 and 46 may be rotated about the pivot points 84 in the direction indicated by the arrow 86 associated therewith by any means known to those skilled in the art. For example, the guides 44 and 46 may simply be allowed to pivot freely as the guides 44 and 46 are oscillated in the cross machine direction 152. Alternatively, the pivoting means 80 may include a second electric motor, such as, for example, a servo motor, operatively connected to the guides 44 and 46 to rotate or pivot the guides about the pivot points 84 in the direction indicated by the arrow 86 associated therewith. In use, the guides 44 and 46 may cyclically rotate or pivot back and forth in the direction indicated by the arrow 86 associated therewith in the y-z plane to maintain the spacing between the elastic strands 22 substantially constant.

The elastic applicating unit 40 of the present invention may further include an elongating means 90 which is positioned along the elastic path 36. The elongating means 90 is configured to elongate the elastic strands 22 before the elastic strands are secured to the substrate 24. As representatively illustrated in FIG. 2, the elongating means 90 may include a pair of variable speed drive rolls 92 and 94. In use, the elastic strands 22 constrictively travel between the drive rolls 92 and 94. The speed of the drive rolls 92 and 94 is then varied to elongate the elastic strands 22 between the drive rolls 92 and 94 and the nip rolls 70 and 72. Alternatively, the elongating means may include a reciprocating block which is located along the elastic path 36 between the drive rolls 92 and 94 and the nip rolls 70 and 72 and is configured to move the elastic strands in a direction transverse to the elastic path in the x-y plane thereby elongating the elastic strands 22 before they are secured to the substrate 24.

The elongating means 90 can be configured to apply either a constant elongation or a variable elongation to the elastic strands 22 before they are secured to the substrate 24. For example, the elastic strands 22 can be elongated from about 50 to about 350 percent and desirably from about 100 to about 250 percent. In a particular aspect of the invention as representatively illustrated in FIG. 1, the elastic strands 22 may be elongated from about 100 to about 250 percent in the region of the substrate 24 where the distance between the curvilinear paths 26 and 28 in the cross machine direction 152 is at a minimum and from about 50 to about 100 percent in the region of the substrate 24 where the distance between the curvilinear paths 26 and 28 in the cross machine direction 152 is at a maximum. Alternatively, if a plurality of elastic strands 22 are used, the elongating means 90 may also be configured to elongate each elastic strand 22 independently of each other.

The different aspects of the apparatus and method of the present invention are configured to apply at least one elastic strand on a continuously moving substrate along a selected curvilinear path. As representatively illustrated in FIG. 1, the curvilinear paths 26 and 28 may be configured to vary through a side-to-side, traversing distance 27 of from about 1 to about 12 centimeters and desirably from about 3 to about 5 centimeters measured along the cross direction 152.

The different aspects of the present invention can also be used to secure a plurality of elastic strands to a moving substrate, such as a diaper web, to provide the leg elastics along the leg opening regions of an absorbent article. The elastic applicating unit 40, as representatively illustrated in FIG. 2, may be used to intermittently apply a plurality of stretched elastic strands 22 to the substrate 24 along the curvilinear paths 26 and 28. For example, the bonding means 62 may intermittently apply an adhesive to the elastic strands 22 or to the substrate 24 before the elastic strands 22 are secured to the substrate 24. After the elastic strands 22 are intermittently secured to the substrate 24, the unsecured portions of the elastic strands 22 may be severed and allowed to contract. Thus, the stretched elastic strands 22 may be intermittently secured to the substrate 24 at selected locations along the curvilinear paths 26 and 28 that correspond to the leg opening regions of the absorbent article.

Figure 4:
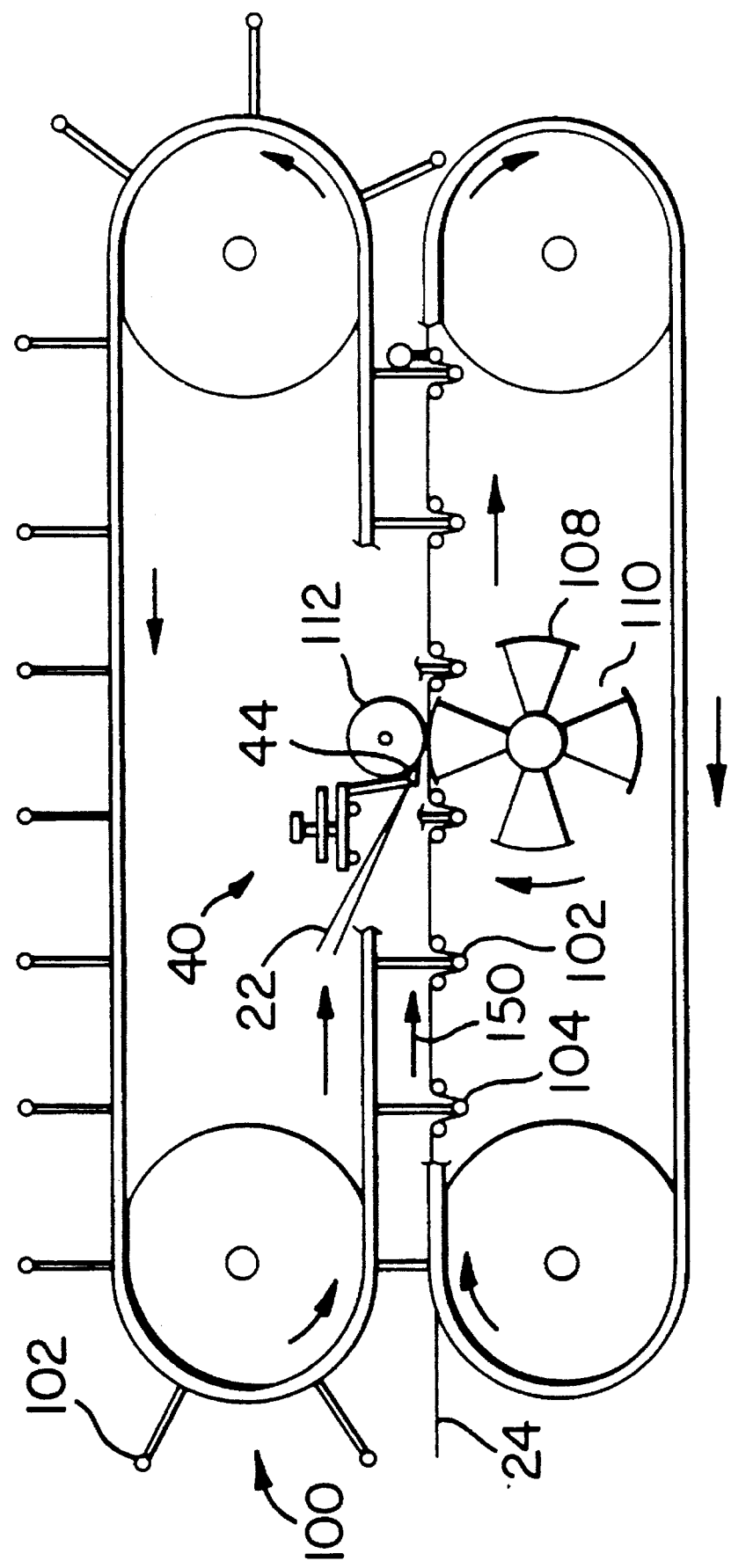
FIG. 4 representatively shows a side elevational view of an apparatus for applying elongated elastic members on a continuously moving substrate along a curvilinear path.

The apparatus and method of the different aspects of the present invention may also be used in combination with other mechanisms to secure at least one elastic strand onto a moving substrate along a curvilinear path. For example, FIG. 4 illustrates a suitable mechanism 100 which incorporates the elastic applicating unit 40 (FIG. 2) of the different aspects of the present invention to secure a plurality of elastic strands onto a moving substrate web, such as a web of diaper articles. The elastic applicating unit 40 may be used to apply leg elastics to each diaper article along curvilinear paths which correspond to the leg opening regions of the diaper.

Figure 5:
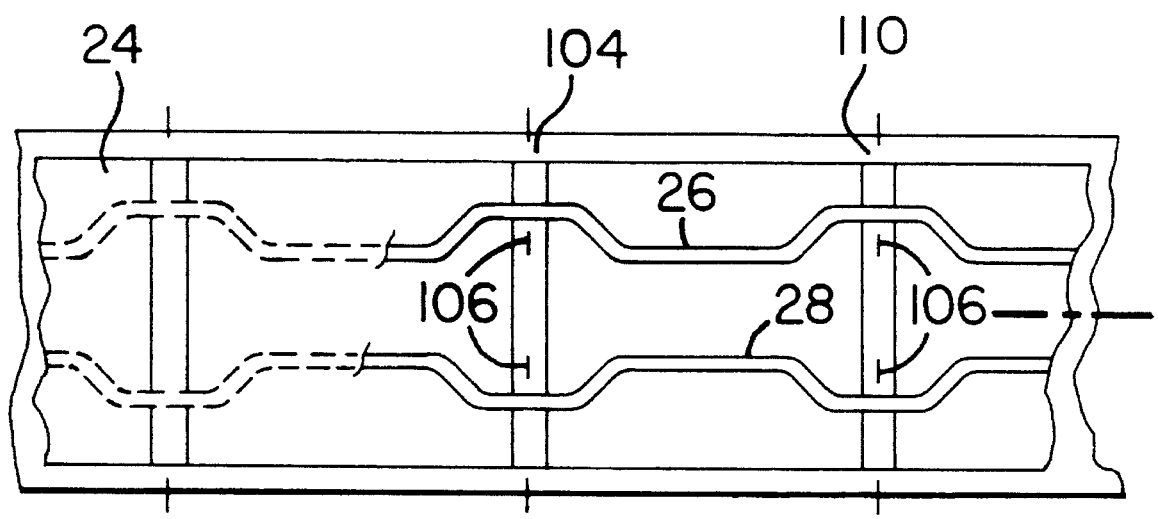
FIG. 5 representatively shows a top plan view of a tucked substrate web onto which elastic members have been placed along a curvilinear path.
Figure 5A:
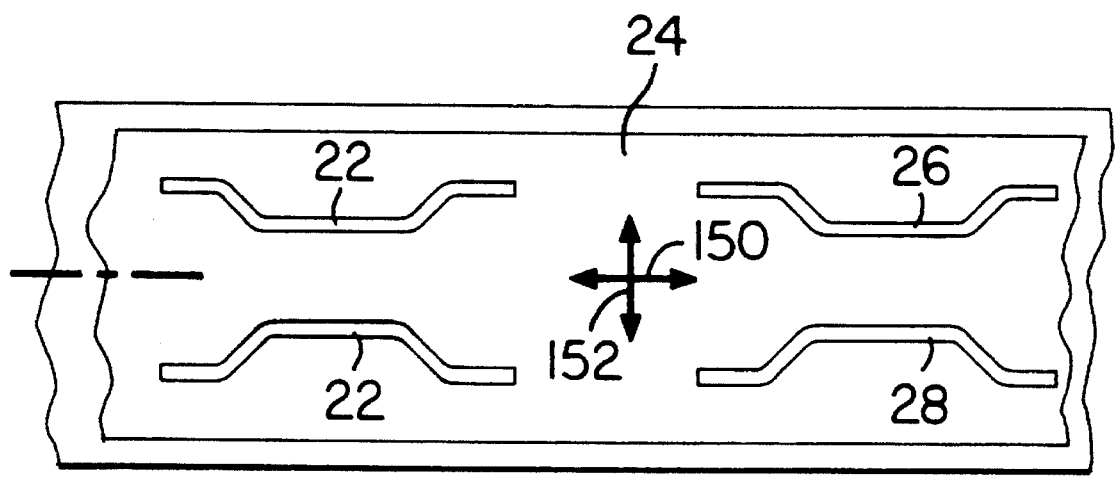
FIG. 5A representatively shows a top plan view of an untucked substrate web onto which elastic members have been placed along a curvilinear path at spaced apart locations.

The mechanism 100 employs a system of tucker bars 102, which form a regularly spaced series of tuck regions 104 in the substrate 24 to provide for an intermittent placement of the elastic strands 22 along the length of the substrate 24. More particularly, the elastic strands 22 are secured to the moving substrate web 24 with discrete sections of the elastic strands 22 bridging across the gaps produced by the plurality of tuck regions 104, as representatively illustrated in FIGS. 4 and 5. After the contacting sections of the elastic strands 22 are secured to the substrate web 24, the bridging elastic sections are severed with a suitable cutting mechanism along appointed separation lines 106 (FIG. 5), and the substrate 24 is then re-extended to operably remove the tuck regions 104. Accordingly, the substrate area incorporated within the previously existing tuck regions will not have elastic strands 22 applied thereon. Only the previously untucked sections of substrate 24 will have the elastic strands 22 applied and secured thereto. As representatively illustrated in FIGS. 5 and 5A, the substrate web 24 will have a selected intermittent placement of elastic strands 22 along curvilinear paths 26 and 28 at spaced apart positions along the length of the substrate 24.

Referring again to FIG. 4, the mechanism 100 includes a tuck drum 108. The illustrated embodiment of the tuck drum 108 includes a series of recess regions 110 which are substantially equally spaced along the circumferential peripheral surface of the tuck drum 108. The recess regions 110 are constructed to accommodate the passage of the tucker bars 102 which are employed to form tucks along the length of the substrate 24. The tuck drum 108 provides a complementary nipping roll which cooperates with the nip roll 112 to position and press the elastic strands 22 against the substrate 24 to maintain the elastic strands along the preselected curvilinear paths 26 and 28. In the illustrated embodiment, the elastic applicating unit 40 is positioned in close proximity to the tuck drum 108 such that the guides 44 and 46 are configured to direct the elastic strands 22 onto the substrate 24 along the curvilinear paths 26 and 28 between the tuck drum 108 and nip roll 112. As discussed above, it is desirable that the guides 44 and 46 are within at least about 5 centimeters and desirably within at least about 1 centimeter of the substrate 24 to ensure that the elastic strands 22 follow the curvilinear paths 26 and 28.

The tuck drum 108 is suitably mounted on a shaft to be rotatable about an axis. The drum is also operatively driven such that the peripheral, surface speed of the tuck drum 108 substantially matches the speed at which the substrate 24 is moving along the machine direction 150 through the elastic applicating unit 40.

As discussed above, FIG. 6 representatively illustrates an absorbent article 200 which may include elastic members which can be applied using the method and apparatus according to the various aspects of the present invention. The absorbent article will be described in terms of a diaper article adapted to be worn by infants about the lower torso. However, it is understood that the present invention is equally applicable to other absorbent articles such as adult incontinent products, training pants, feminine care products and the like. As representatively illustrated in FIG. 6, the absorbent article 200 defines a front portion 202, a rear portion 204, and a crotch portion 206 connecting the front portion 202 and the rear portion 204. The absorbent article 200 includes a bodyside liner 210, an outer cover 212 and an absorbent core 214 located between the bodyside liner 210 and the outer cover 212. As used herein, reference to a front portion refers to that part of the absorbent article which is generally located on the front of a wearer when in use. Reference to the rear portion refers to the portion of the article generally located at the rear of the wearer when in use, and reference to the crotch portion refers to that portion which is generally located between the legs of the wearer when in use.

The crotch portion 206 has opposite longitudinal side portions 208 which include a pair of elasticized, longitudinally-extending leg cuffs 216. The leg cuffs 216 are generally adapted to fit about the legs of a wearer in use and serve as a mechanical barrier to the lateral flow of body exudates. The leg cuffs 216 are elasticized by a pair of leg elastics 218. The absorbent article 200 further includes a front waist elastic 220 and a rear waist elastic 222. The rear portion 204 of the absorbent article 200 further includes a fastening means, such as a pair of tape fasteners 224. The tape fasteners 224 are intended to hold the absorbent article 200 about the waist of the wearer when in use.

Figure 6:
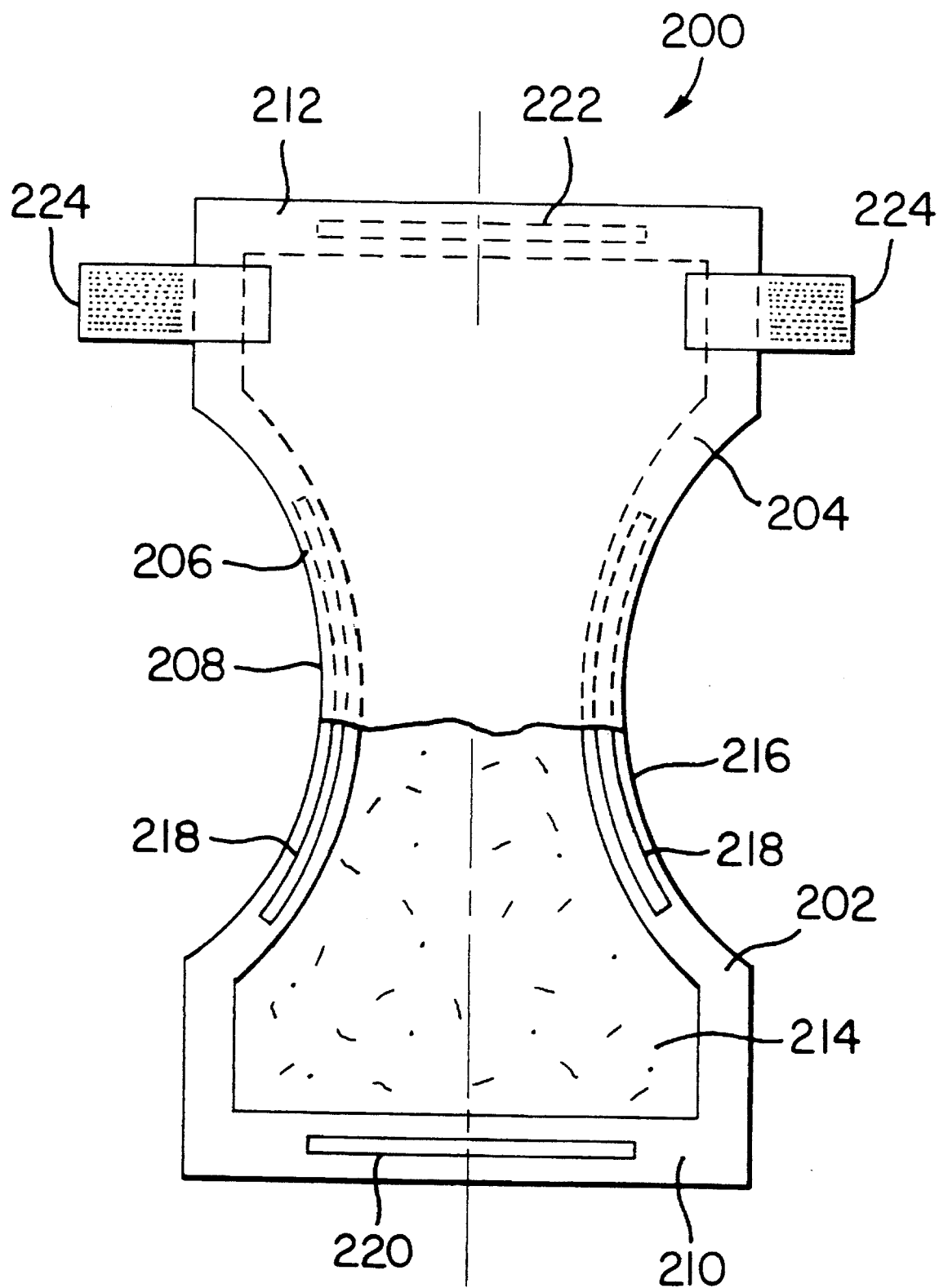
FIG. 6 representatively shows a partially cut away, plan view of a diaper article which incorporates a pair of curved elastic members for elasticizing the leg openings at the side margins of the article.

The bodyside liner 210 of the absorbent article 200, as representatively illustrated in FIG. 6, suitably presents a bodyfacing surface which is compliant, soft feeling and nonirritating to the wearer's skin. Further, the bodyside liner 210 may be less hydrophilic than the absorbent core 214, to present a relatively dry surface to the wearer, and may be sufficiently porous to be liquid permeable, permitting liquid to readily penetrate through its thickness. A suitable bodyside liner 210 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 210 is suitably employed to help isolate the wearer's skin from liquids held in the absorbent core 214.

Various woven and nonwoven fabrics can be used for the bodyside liner 210. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 210 comprises a nonwoven, spunbond, polypropylene fabric composed of about 2.8–3.2 denier fibers formed into a web having a basis weight of about 22 grams per square meter and a density of about 0.06 gram per cubic centimeter. The fabric is surface treated with about 0.28 weight percent of a surfactant commercially available from Rohm and Haas Co. under the trade designation Triton X-102.

The outer cover 212 of the absorbent article 200, as representatively illustrated in FIG. 6, may suitably be composed of a material which is either liquid permeable or liquid impermeable. It is generally preferred that the outer cover 212 be formed from a material which is substantially impermeable to liquids. For example, a typical outer cover can be manufactured from a thin plastic film or other flexible liquid-impermeable material. For example, the outer cover 212 may be formed from a polyethylene film having a thickness of from about 0.012 millimeter (0.5 mil) to about 0.051 millimeter (2.0 mils). If it is desired to present the outer cover 212 with a more clothlike feeling, the outer cover 212 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover 212 may be formed of a woven or nonwoven fibrous web layer which has been totally or partially constructed or treated to impart a desired level of liquid impermeability to selected regions that are adjacent or proximate the absorbent core 214. Still further, the outer cover 212 may optionally be composed of a micro-porous "breathable" material which permits vapors to escape from the absorbent core 214 while still preventing liquid exudates from passing through the outer cover 212.

The absorbent core 214 of the absorbent article 200, as representatively illustrated in FIG. 6, may suitably comprise a matrix of hydrophilic fibers, such as a web of cellulosic fluff, mixed with particles of a high-absorbency material commonly known as superabsorbent material. In a particular embodiment, the absorbent core 214 comprises a mixture of superabsorbent hydrogel-forming particles and wood pulp fluff. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent core 214 may comprise a laminate of fibrous webs and superabsorbent material or other suitable means of maintaining a superabsorbent material in a localized area.

The absorbent core 214 may have any of a number of shapes. For example, the absorbent core may be rectangular, I-shaped or T-shaped. It is generally preferred that the absorbent core be narrower in the crotch portion 206 of the absorbent article 200 than in the front or rear portion, 202 or 204, respectively.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent core in an amount of from about 5 to about 100 weight percent based on total weight of the absorbent core 214.

The outer cover 212 and bodyside liner 210 are generally adhered to one another so as to form a pocket in which the absorbent core 214 is located. Thus, the leg cuffs 216 are suitably formed by portions of the outer cover 212, and/or bodyside liner 210, which extend beyond the longitudinal sides of the absorbent core 214. Naturally, the leg cuffs 216 can also be formed from separate materials which are attached to the outer cover 212 and/or bodyside liner 210.

The leg cuffs 216, as representatively illustrated in FIG. 6, include leg elastics 218. Materials suitable for use in forming leg elastics 218 are known to those skilled in the art. Exemplary of such materials are strands or ribbons of a polymeric, elastomeric material which are adhered to the absorbent article 200 at the leg cuffs 216 while in a stretched position, or which are attached to the absorbent article while the article is pleated, such that elastic constrictive forces are imparted to the leg cuffs 216. Waist elastics 220 and 222 and tape fasteners 224, as representatively illustrated in FIG. 6, are also known to those skilled in the art.

As representatively illustrated in FIG. 6, the leg elastics 218 may be curved to more closely fit the contours of the legs and buttocks of the wearer and better contain bodily exudates. The curved leg elastics 218 may include a plurality of elastic strands that are intermittently applied to the article 200 using the method and apparatus of the various aspects of the present invention such as, for example, the apparatus illustrated in FIGS. 2 and 4. For example, the elastic strands may be intermittently applied to the outer cover 212 using the mechanism illustrated in FIG. 4 which incorporates the apparatus and method of the different aspects of the present invention. The outer cover 212 with the intermittently applied elastic strands may then be adhered to the bodyside liner 210 with the absorbent core 214 disposed therebetween. The elastic strands are selectively located along the leg opening regions of each absorbent article 200 to provide the leg elastics 218.

Having thus described the invention in rather full detail, it is readily apparent that various changes and modifications can be made without departing from the spirit of the invention. All of such changes and modifications are contemplated as being within the scope of the present invention, as defined by the subjoined claims.

What is claimed is:

1. A method for applying at least one elastic strand onto a continuously moving substrate along a curvilinear path, said method comprising the steps of:

a) moving said substrate along a substrate path;

b) supplying said elastic strand along an elastic path;

c) delivering said elastic strand to said substrate along said curvilinear path wherein said delivering step includes the step of moving said elastic strand with a slidably movable guide in a direction essentially transverse to said substrate path, said guide having at least one groove therein having a depth of from about 0.5 to about 2 centimeters and a length of at least about 3 centimeters to contain and slidably move said elastic strand;

d) applying an adhesive in an arrangement which secures said elastic strand to said substrate along said curvilinear path; and e) pressing said elastic strand onto said substrate with at least one rotatable nip roll to maintain said elastic strand on said substrate along said curvilinear path.

2. The method as recited in claim 1 and further comprising the step of elongating said elastic strand before said elastic strand is secured to said substrate, said elongating provided by constrictively passing said elastic strand between a pair of drive rolls and rotating said drive rolls at a variable speed to variably elongate said elastic strand.

3. The method as recited in claim 2 wherein said elongating step includes the step of elongating said elastic strand from about 50 to about 350 percent.

4. The method as recited in claim 1 wherein said applying step includes the step of depositing said adhesive onto said elastic strand before said elastic strand contacts said substrate.

5. The method as recited in claim 4 wherein said applying step includes the step of depositing said adhesive to substantially cover an outer peripheral surface of said elastic strand.

6. The method as recited in claim 1 wherein said delivering step includes the steps of providing a plurality of from 1 to about 10 elastic strands and providing a plurality of grooves in said guide to slidably move said elastic strands.

7. The method as recited in claim 6 wherein said delivering step further includes the step of rotating said guide as said guide moves to maintain a substantially constant spacing between said elastic strands as said elastic strands are delivered and pressed onto said substrate web along said curvilinear path.

8. The method as recited in claim 1 wherein a distance between said guide and a position where said elastic strand contacts said substrate is from about 0.25 to about 5 centimeters.

9. An apparatus for applying at least one elastic strand onto a continuously moving substrate along a selected curvilinear path, said apparatus comprising:

a) a transporting means for moving said substrate along a substrate path;

b) a supplying means for providing said elastic strand along an elastic path;

c) an oscillating means for selectively changing a positioning of said elastic strand, said oscillating means including a slidably movable guide which is located along said elastic path and which includes at least one groove therein in a direction essentially parallel to said elastic path, said groove having a length of at least about 3 centimeters and a depth of from about 0.5 to about 2 centimeters to contain and slidably guide said elastic strand wherein said guide is configured to slidably move in a direction essentially transverse to said substrate path such that said elastic strand follows said curvilinear path;

d) a bonding means for selectively applying an adhesive in an arrangement which secures said elastic strand to said substrate along said curvilinear path; and e) a pair of rotatable nip rolls which are adapted to be in rolling engagement with said substrate and which are configured to press said elastic strand onto said substrate to maintain said elastic strand on said substrate along said curvilinear path.

10. The apparatus as recited in claim 9 wherein said groove in said guide has a length of from about 4 to about 8 centimeters.

11. The apparatus as recited in claim 9 wherein said guide is made from a polytetrafluoroethylene material.

12. The apparatus as recited in claim 1 wherein said guide has a plurality of grooves therein in a direction essentially parallel to said elastic path, said grooves having a depth sufficient to contain and slidably guide a plurality of said elastic strands as said guide moves.

13. The apparatus as recited in claim 12 wherein said oscillating means further includes a pivoting means for selectively rotating said guide as said guide moves.

14. The apparatus as recited in claim 12 wherein said rotating of said guide maintains a substantially constant spacing between said elastic strands as said elastic strands are secured to said substrate along said curvilinear path.

15. The apparatus as recited in claim 9, further comprising an elongating means positioned along said elastic path for variably elongating said elastic strand before said elastic strand is selectively secured to said substrate.

16. The apparatus as recited in claim 15 wherein said elongating means comprises a pair of variable speed drive rolls through which said elastic strand constrictively travels, said drive rolls rotating at a variable speed to variably elongate said elastic strand.

17. An apparatus for applying a first plurality of elastic strands onto a substrate along a first curvilinear path and a second plurality of elastic strands onto said substrate along a second curvilinear path, said apparatus comprising:

a) a transporting means for moving said substrate along a substrate path;

b) a supplying means for providing said first and said second plurality of elastic strands along an elastic path;

c) a rotatable cam;

d) a first slidably movable guide which is located along said elastic path and which includes a plurality of grooves therein in a direction essentially parallel to said elastic path, said grooves having a length of at least about 3 centimeters and a depth of from about 0.5 to about 2 centimeters to contain and slidably guide said first plurality of elastic strands wherein said first guide further includes a first cam follower which cooperates with said cam wherein said first guide is configured to slidably move in a direction essentially transverse to said substrate path as said cam rotates such that said first plurality of elastic strands follows said first curvilinear path;

e) a second slidably movable guide located along said elastic path and which includes a plurality of grooves therein in a direction essentially parallel to said elastic path, said grooves having a length of at least about 3 centimeters and a depth of from about 0.5 to about 2 centimeters to contain and slidably guide said second plurality of elastic strands wherein said second guide further includes a second cam follower which cooperates with said cam where said second guide is configured to slidably move in a direction essentially transverse to said substrate path as said cam rotates such that said second plurality of elastic strands follows said second curvilinear path;

f) a bonding means for applying an adhesive in an arrangement which selectively secures said first plurality of elastic strands to said substrate along said first curvilinear path and said second plurality of elastic strands to said substrate along said second curvilinear paths; and g) a pair of rotatable nip rolls which are adapted to be in rolling engagement with said substrate and which are configured to press said first and said second plurality of elastic strands onto said substrate to maintain said first plurality of elastic strands on said substrate along said first curvilinear path and to maintain said second plurality of elastic strands on said substrate along said second curvilinear path.

18. The apparatus as recited in claim 17 wherein said first guide and said second guide are capable of simultaneously slidably moving in opposing directions and are located along said elastic path such that a distance between said first and said second guides and a position where said first and said second plurality of elastic strands contact said substrate is from about 0.25 to about 11 centimeters.

19. The apparatus as recited in claim 9 wherein a distance between said guide and a position where said elastic strand contacts said substrate is from about 0.25 to about 5 centimeters.

20. The apparatus as recited in claim 9 wherein a distance between said guide and a position where said elastic strand contacts said substrate is less than 2 centimeters.

\* \* \* \* \*